US006991599B2

(12) United States Patent
Hudson

(10) Patent No.: US 6,991,599 B2
(45) Date of Patent: Jan. 31, 2006

(54) PERSONAL EXERCISE SYSTEM

(76) Inventor: Donald E. Hudson, 5830 Bahia Way South, St. Pete Beach, FL (US) 33706

( * ) Notice: Subject to any disclaimer, the term of this patent is extended or adjusted under 35 U.S.C. 154(b) by 135 days.

(21) Appl. No.: 10/786,268

(22) Filed: Feb. 25, 2004

(65) Prior Publication Data

US 2005/0187431 A1 Aug. 25, 2005

(51) Int. Cl.
*A61F 5/00* (2006.01)

(52) U.S. Cl. ........................................................ 600/38

(58) Field of Classification Search ............ 600/38–41; 5/652, 657, 929; 128/845

See application file for complete search history.

(56) References Cited

U.S. PATENT DOCUMENTS 6,179,795 B1 * 1/2001 Garza .......................... 601/97
6,899,671 B1 * 5/2005 Fontenot ...................... 600/38

* cited by examiner

*Primary Examiner*—Samuel G. Gilbert
(74) *Attorney, Agent, or Firm*—Edward P. Dutkiewicz

(57) ABSTRACT

A coupling component has laterally and rearwardly extending ends. An intermediate component has free lower and upper ends. A dildo is located above the rearwardly extending end. The dildo has an interior end and a free exterior end located above the rearwardly extending end of the coupling component removably coupling the upper intermediate component to the dildo. A handle extends outwardly and upwardly from each laterally extending end of the coupling component.

10 Claims, 6 Drawing Sheets

FIG 4
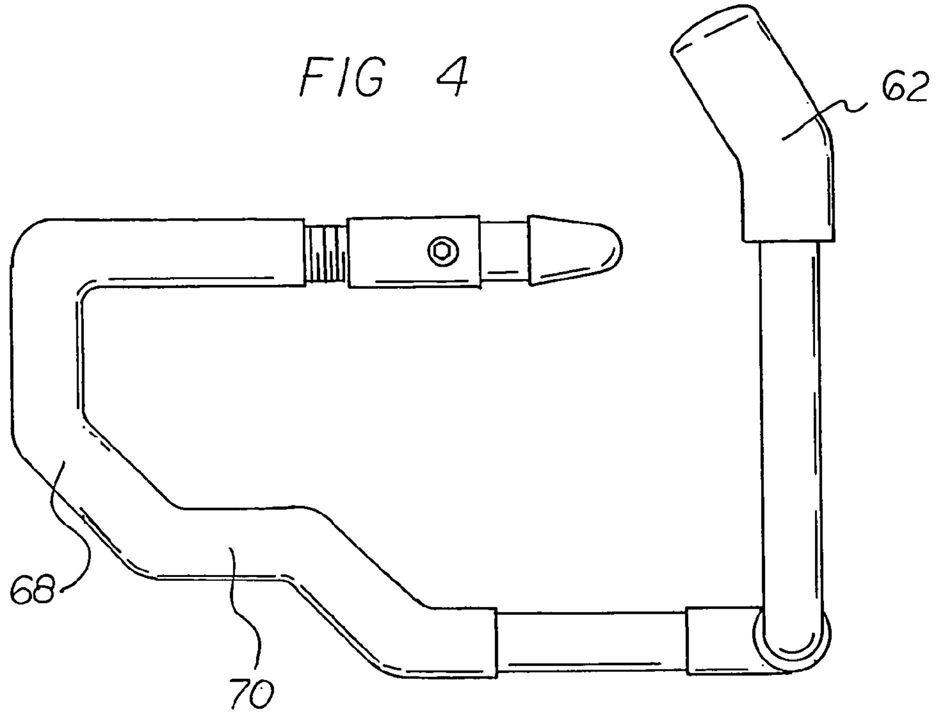
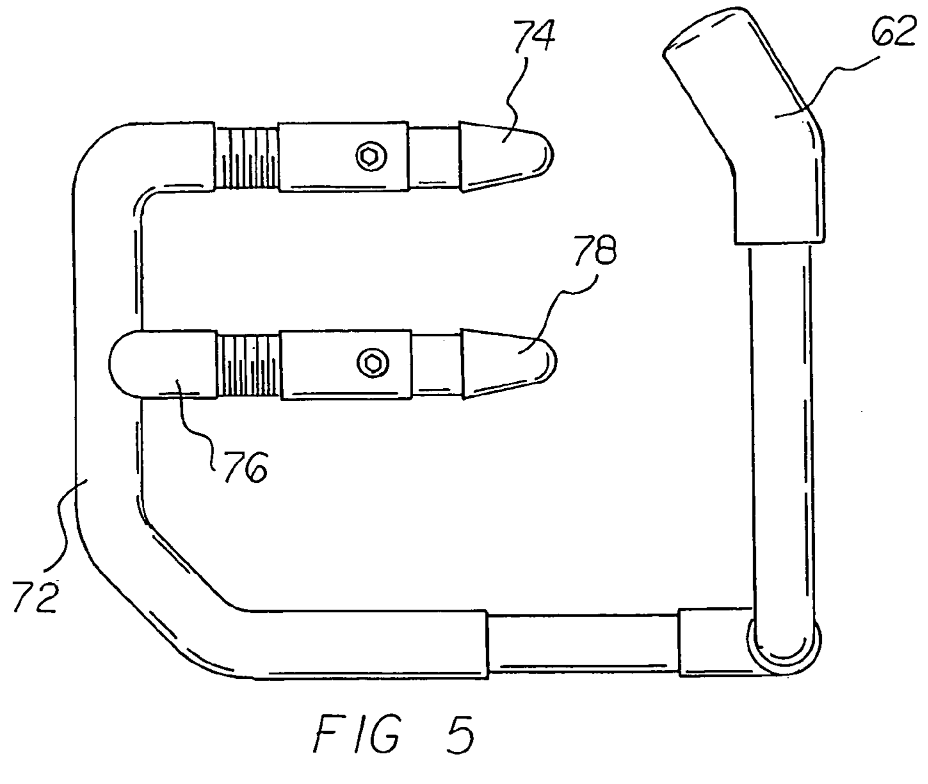
FIG 5

FIG 8
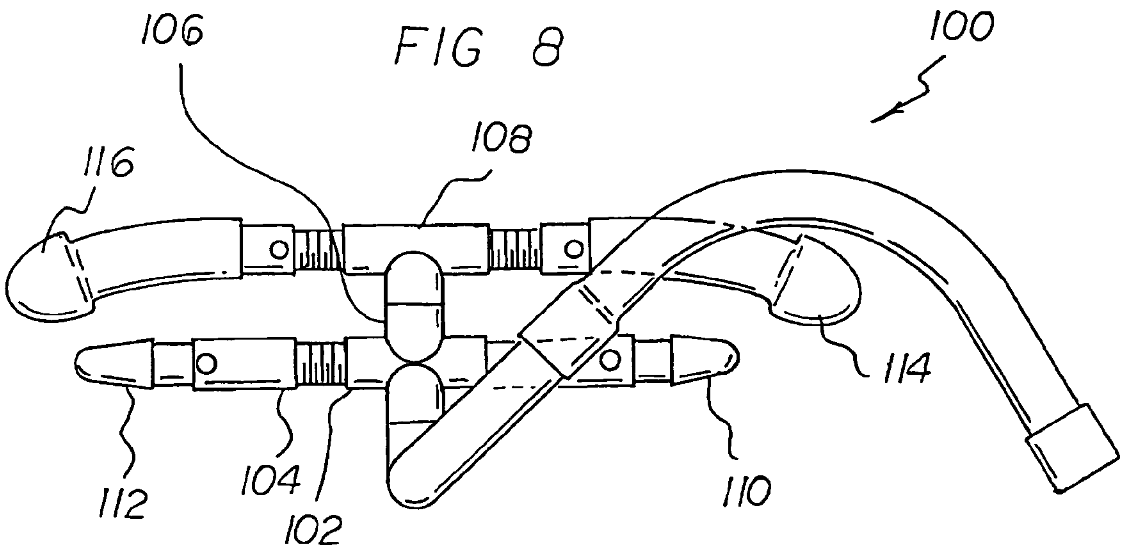
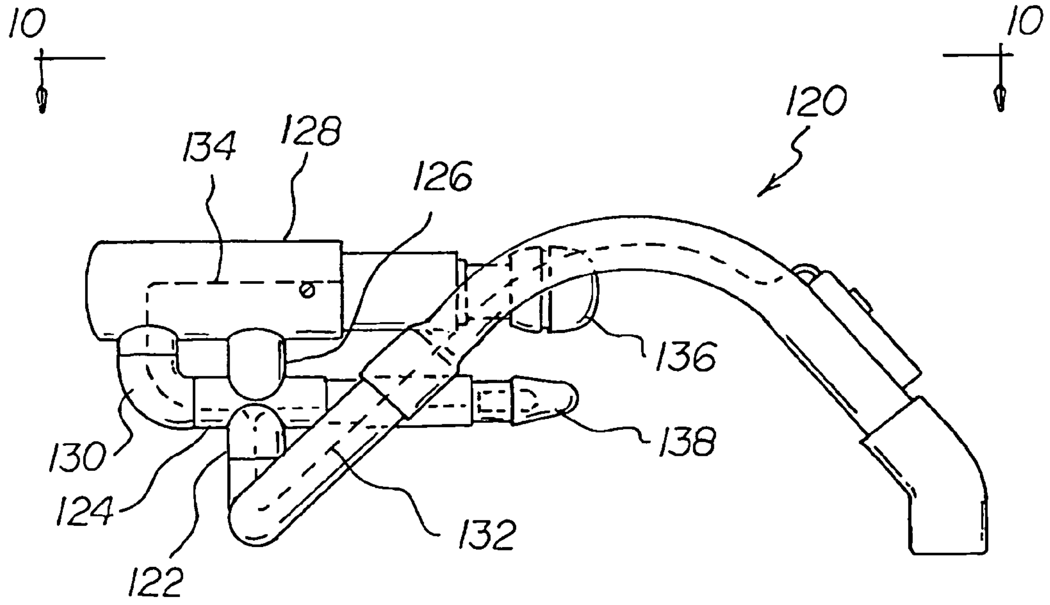
FIG 9

PERSONAL EXERCISE SYSTEM

BACKGROUND OF THE INVENTION

1. Field of the Invention

The present invention relates to a personal exercise system and more particularly pertains to for allowing a user to perform a sexual exercise in a stimulating and healthful manner.

2. Description of the Prior Art

The use of exercise systems of known designs and configurations is known in the prior art. More specifically, exercise systems of known designs and configurations previously devised and utilized for the purpose of performing exercises with conventional methods and apparatuses are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,790,296 issued Dec. 13, 1988 to Segal relates to a sexual stimulation apparatus. U.S. Pat. No. 5,853,362 issued Dec. 29, 1998 to Jacobs relates to a glandular stimulator device and method. Lastly, U.S. Pat. No. 46,540,667 issued Apr. 1, 2003 to Hickman relates to a marital aid.

While these devices fulfill their respective, particular objectives and requirements, the aforementioned patents do not describe personal exercise system that allows for allowing a user to perform a sexual exercise in a stimulating and healthful manner.

In this respect, the personal exercise system according to the present invention substantially departs from the conventional concepts and designs of the prior art, and in doing so provides an apparatus primarily developed for the purpose of for allowing a user to perform a sexual exercise in a stimulating and healthful manner.

Therefore, it can be appreciated that there exists a continuing need for a new and improved personal exercise system which can be used for allowing a user to perform a sexual exercise in a stimulating and healthful manner. In this regard, the present invention substantially fulfills this need.

SUMMARY OF THE INVENTION

In view of the foregoing disadvantages inherent in the known types of exercise systems of known designs and configurations now present in the prior art, the present invention provides an improved personal exercise system. As such, the general purpose of the present invention, which will be described subsequently in greater detail, is to provide a new and improved personal exercise system and method which has all the advantages of the prior art and none of the disadvantages.

To attain this, the present invention essentially comprises a T-shaped coupling component. The coupling component has laterally extending ends and a rearwardly extending end. The coupling component is positionable on a horizontal support surface adjacent to a user.

A U-shaped intermediate component is provided. The intermediate component is in a vertical plane. The intermediate component has a free lower end and a free upper end. The intermediate component is formed with male threads. A lower joining piece is provided. The lower joining piece connects the lower end of the intermediate component and the rearwardly extending end of the coupling component.

Provided next is generally cone shaped dildo. The dildo is in a generally linear configuration located above, and parallel with, the rearwardly extending end and the lower joining piece. The dildo has an interior end and a free exterior end located above the rearwardly extending end of the T-shaped coupling component. An upper joining piece is provided. The upper joining piece has a rearward end. The rearward end is formed with female threads. The female threads on the rearward end are removably coupled to the male threads of the intermediate component. The upper joining piece has a forward end. The forward end is formed with a set screw. The set screw is for removably securing the dildo and the upper joining piece to the male threads of the intermediate component.

A handle is provided next. The handle extends outwardly and upwardly from each laterally extending end of the T-shaped coupling component. Each handle has an upper arcuate portion. The upper arcuate portion has a free upper end and a lower linear component. The lower linear component has an interior end. The interior end is coupled to a laterally extending end of the T-shaped coupling component. The handle and laterally extending ends of the T-shaped coupling component are located in a vertical plane perpendicular to the horizontal plane containing the intermediate member.

Further provided is a grip. The grip is fabricated of an elastomeric material. The elastomeric material is rubber or plastic, natural or synthetic, or blends thereof. The grip is removably positioned on each free end of the handle. Each grip extends upwardly and rearwardly away from the vertical plane containing the handle. The grips are at an elevation above the dildo. The free end of the dildo is at an elevation adjacent to the midpoint of the arcuate portion of the handle.

Provided last is a supplemental dildo. The supplemental dildo has a hemispherical free end. The supplemental dildo is adapted to be used as an alternative to the dildo with the generally conical free end.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved personal exercise system which has all of the advantages of the prior art exercise systems of known designs and configurations and none of the disadvantages.

It is another object of the present invention to provide a new and improved personal exercise system which may be easily and efficiently manufactured and marketed.

It is further object of the present invention to provide a new and improved personal exercise system which is of durable and reliable constructions.

An even further object of the present invention is to provide a new and improved personal exercise system which is susceptible of a low cost of manufacture with regard to both materials and labor, and which accordingly is then susceptible of low prices of sale to the consuming public, thereby making such personal exercise system economically available to the buying public.

Even still another object of the present invention is to provide a personal exercise system for for allowing a user to perform a sexual exercise in a stimulating and healthful manner.

Lastly, it is an object of the present invention to provide a new and improved personal exercise system. A coupling component has laterally and rearwardly extending ends. An intermediate component has free lower and upper ends. A dildo is located above the rearwardly extending end. The dildo has an interior end and a free exterior end located above the rearwardly extending end of the coupling component removably coupling the upper intermediate component to the dildo. A handle extends outwardly and upwardly from each laterally extending end of the coupling component.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 4 is a side elevational view similar to FIG. 2 but illustrating an alternate embodiment of the invention.

FIG. 5 is a side elevational view similar to FIGS. 2 and 4 but illustrating another alternate embodiment of the invention.

FIG. 8 is a side elevational view of an even further alternate embodiment of the invention.

FIG. 9 is a side elevational view of the final alternate embodiment of the invention.

The same reference numerals refer to the same parts throughout the various Figures.

DESCRIPTION OF THE PREFERRED EMBODIMENT

Figure 1:
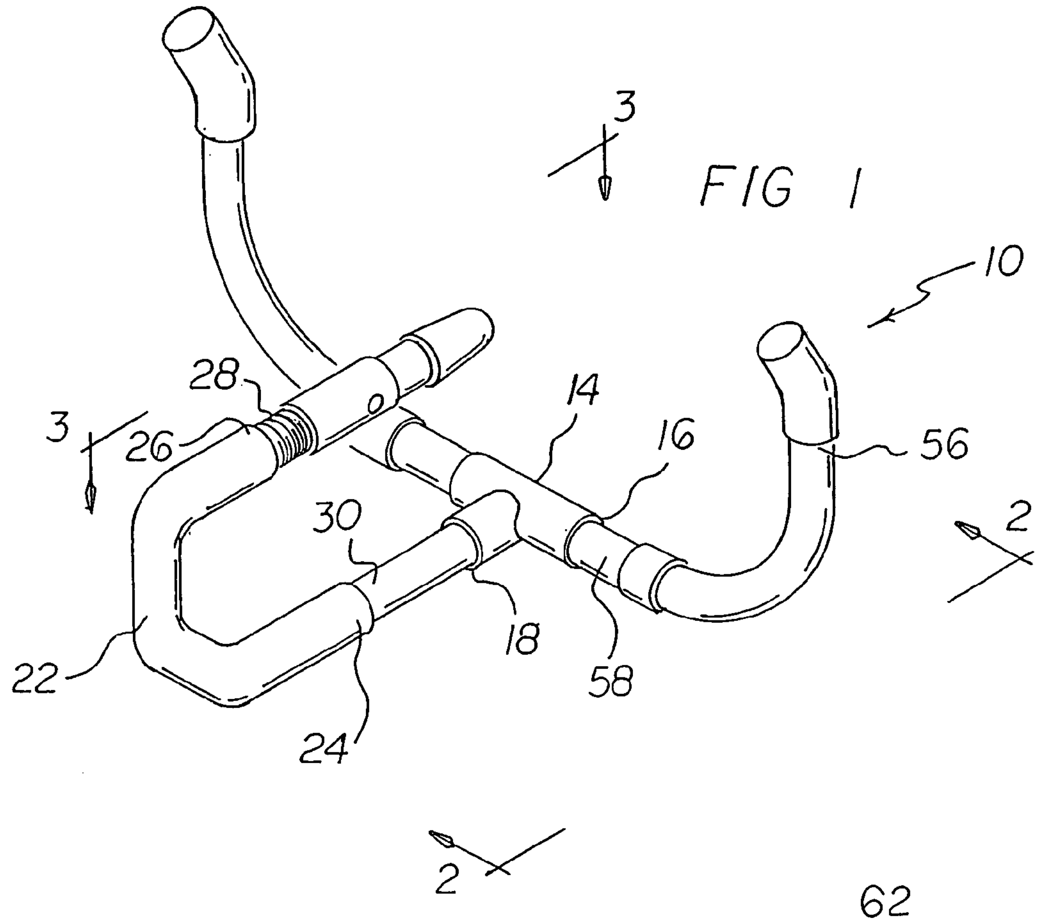
FIG. 1 is a perspective showing of a personal exercise system constructed in accordance with the principles of the present invention.
Figure 2:
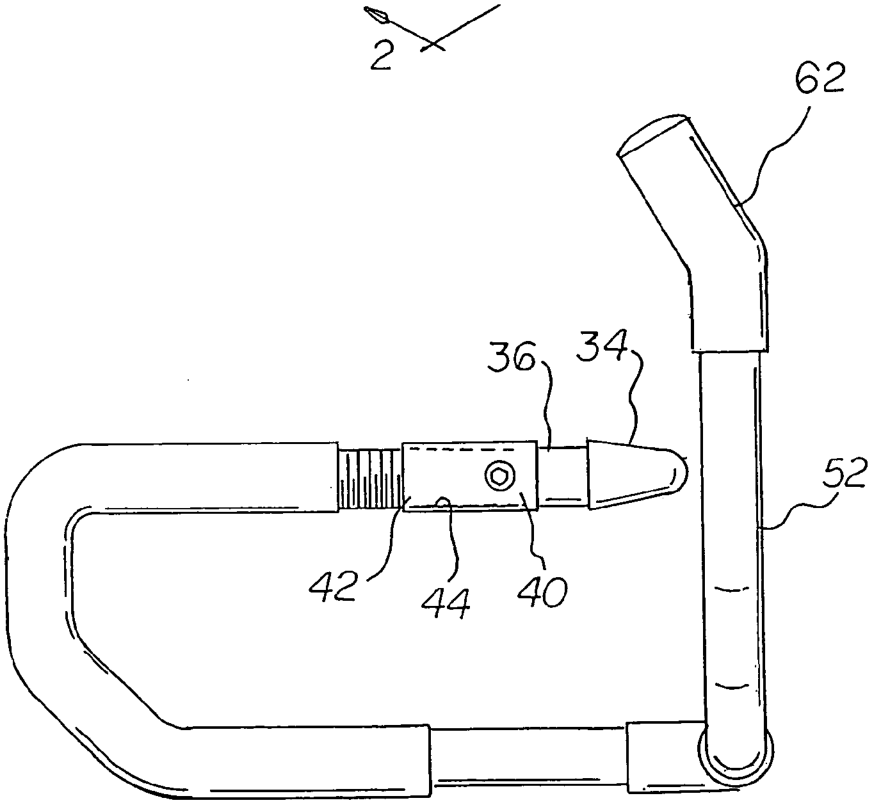
FIG. 2 is a side elevational view taken along line 2—2 of FIG. 1.
Figure 3:
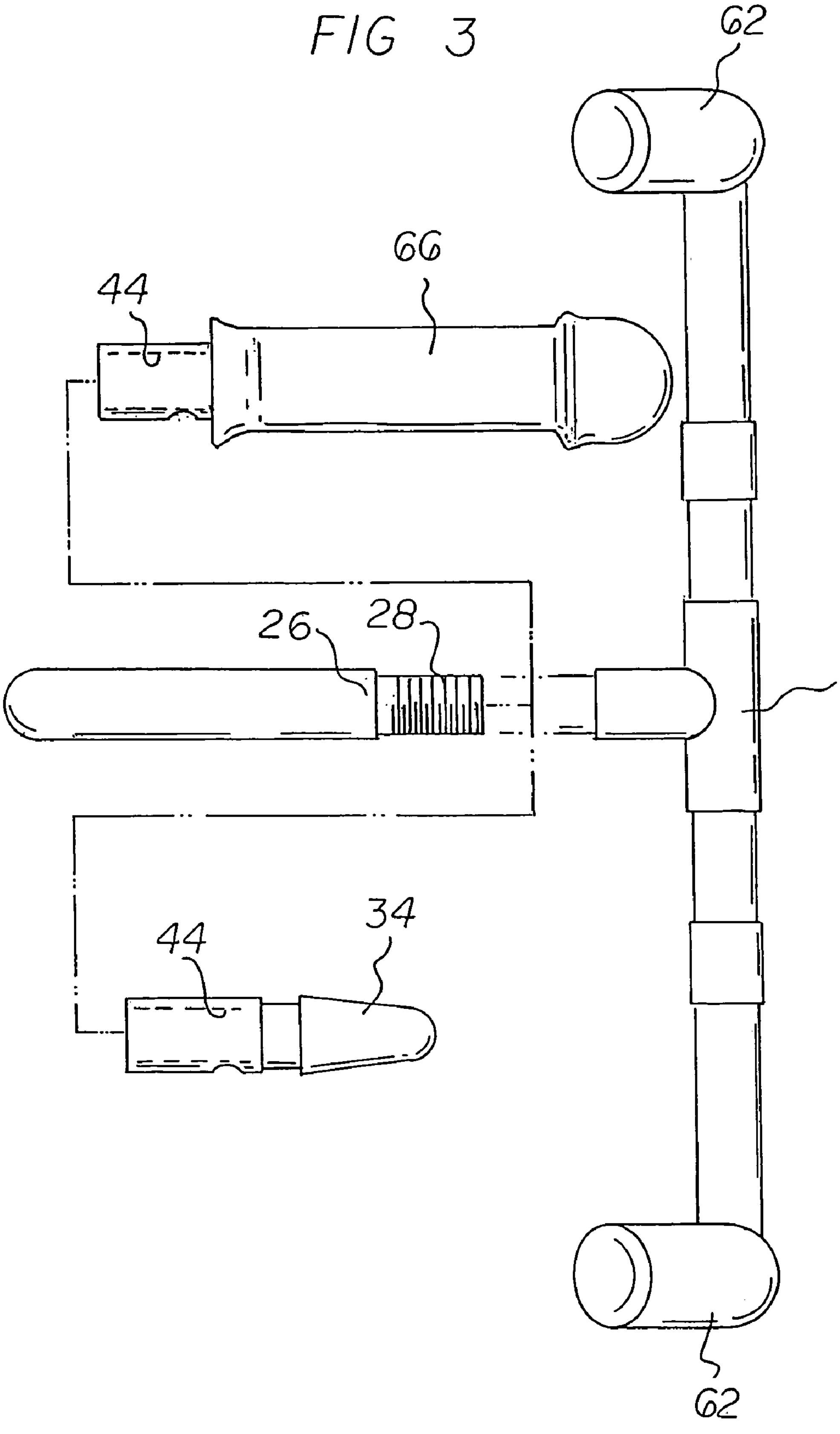
FIG. 3 is a front elevational view, partially exploded, taken along line 3—3 of FIG. 1.

With reference now to the drawings, and in particular to FIG. 1 thereof, the preferred embodiment of the new and improved personal exercise system embodying the principles and concepts of the present invention and generally designated by the reference numeral 10 will be described.

The present invention, the personal exercise system 10 is comprised of a plurality of components. Such components in their broadest context include a coupling component, an intermediate component, a dildo, a handle, and a grip. Such components are individually configured and correlated with respect to each other so as to attain the desired objective.

First provided is a T-shaped coupling component 14. The coupling component has laterally extending ends 16 and a rearwardly extending end 18. The coupling component is positionable on a horizontal support surface adjacent to a user.

A U-shaped intermediate component 22 is provided. The intermediate component is in a vertical plane. The intermediate component has a free lower end 24 and a free upper end 26. The intermediate component is formed with male threads 28. A lower joining piece 30 is provided. The lower joining piece connects the lower end of the intermediate component and the rearwardly extending end of the coupling component.

Provided next is generally cone shaped dildo 34. The dildo is in a generally linear configuration located above, and parallel with, the rearwardly extending end and the lower joining piece. The dildo has an interior end 36 and a free exterior end 38 located above the rearwardly extending end of the T-shaped coupling component. An upper joining piece 40 is provided. The upper joining piece has a rearward end 42. The rearward end is formed with female threads 44. The female threads on the rearward end are removably coupled to the male threads of the intermediate component. The upper joining piece has a forward end 46. The forward end is formed with a set screw 48. The set screw is for removably securing the dildo and upper joining piece to the male threads of the intermediate component.

A handle 52 is provided next. The handle extends outwardly and upwardly from each laterally extending end of the T-shaped coupling component. Each handle has an upper arcuate portion 54. The upper arcuate portion has a free upper end 56 and a lower linear component 58. The lower linear component has an interior end. The interior end is coupled to a laterally extending end of the T-shaped coupling component. The handle and laterally extending ends of the T-shaped coupling component are located in a vertical plane perpendicular to the horizontal plane containing the intermediate member.

Further provided is a grip 62. The grip is fabricated of an elastomeric material. The elastomeric material is rubber or plastic, natural or synthetic, or blends thereof. The grip is removably positioned on each free end of the handle. Each grip extends upwardly and rearwardly away from the vertical plane containing the handle. The grips are at an elevation above the dildo. The free end of the dildo is at an elevation adjacent to the midpoint of the arcuate portion of the handle.

Provided last is a supplemental dildo 66. The supplemental dildo has a hemispherical free end. The supplemental dildo is adapted to be used as an alternative to the dildo with the generally conical free end.

An alternate embodiment of the invention can be seen in FIG. 4. In such embodiment, there is included a grip. The grip is positioned on each upper free ends of the handle remote from the coupling component. The intermediate component 68 is formed to have a supplemental bend 70 for locating the dildo at an elevated height. Each grip extends upwardly and rearwardly. The grips have a lower end. The lower end is at an elevation adjacent to the dildo.

Another alternate embodiment of the invention can be seen in FIG. 5. In such embodiment, there is included a grip. The grip is positioned on each upper free end of the handle remote from the coupling component. The intermediate component 72 is formed to support an upper dildo 74. A supplemental projection 76 is formed to support a supplemental dildo 78 beneath the upper dildo and for locating the dildos at heights, one above and one below the lower ends of the grips.

Figure 6:
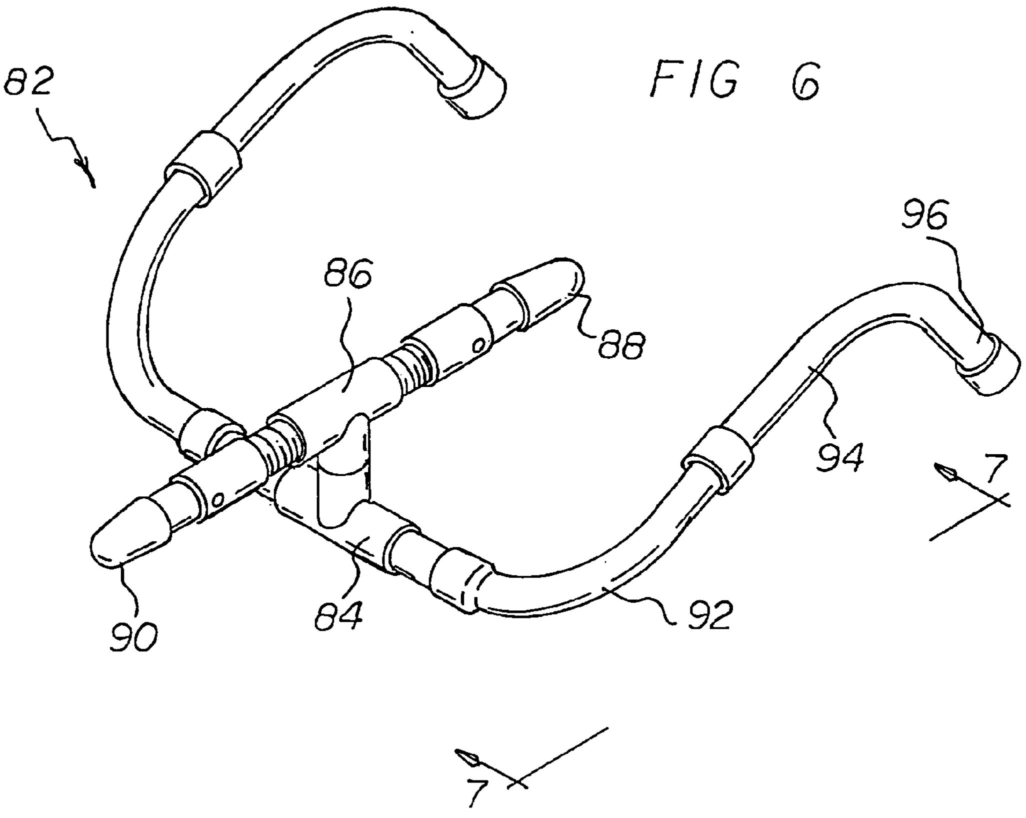
FIG. 6 is a perspective illustration of yet another alternate embodiment of the invention.

FIG. 6 is a perspective illustration of yet another alternate embodiment of the invention. In this embodiment, the system 82 is similar in many respects to that of the embodiments of the prior Figures. The coupling component 84 has laterally extending ends facing sideways for the handles and an upwardly extending end. A supplemental coupling component 86 has longitudinally extending ends facing forwardly and rearwardly and a downwardly extending end coupled to the upwardly extending end. The supplemental coupling component receives a forwardly extending dildo 88 for a primary user and a rearwardly extending dildo for another user. The dildos are in axial alignment. The handles include similarly configured interior components 92 coupled interiorly to the laterally extending ends of the coupling component. The handles also include similarly configured exterior components 96 coupled interiorly to the interior components. The exterior components have generally directed free ends 98 for being held by a primary user.

Figure 7:
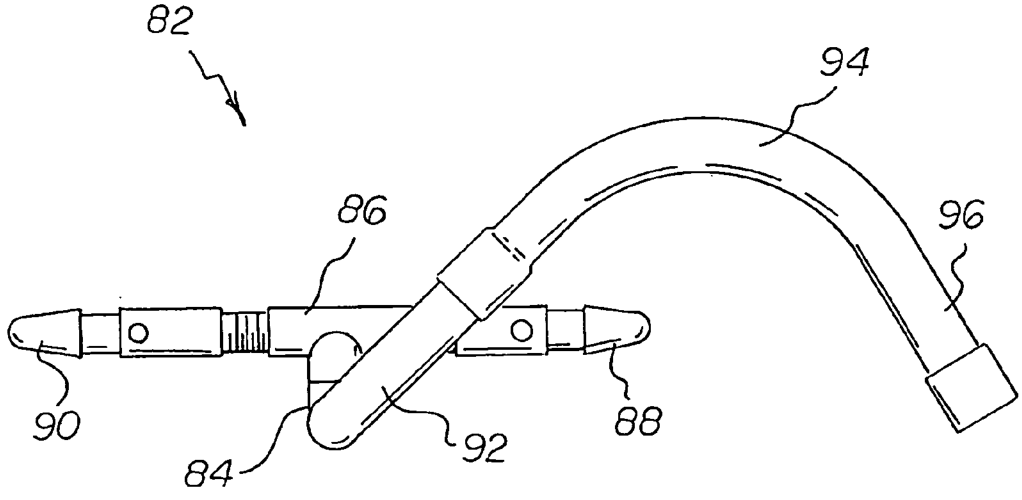
FIG. 7 is a side elevational view taken along line 7—7 of FIG. 6.
Figure 10:
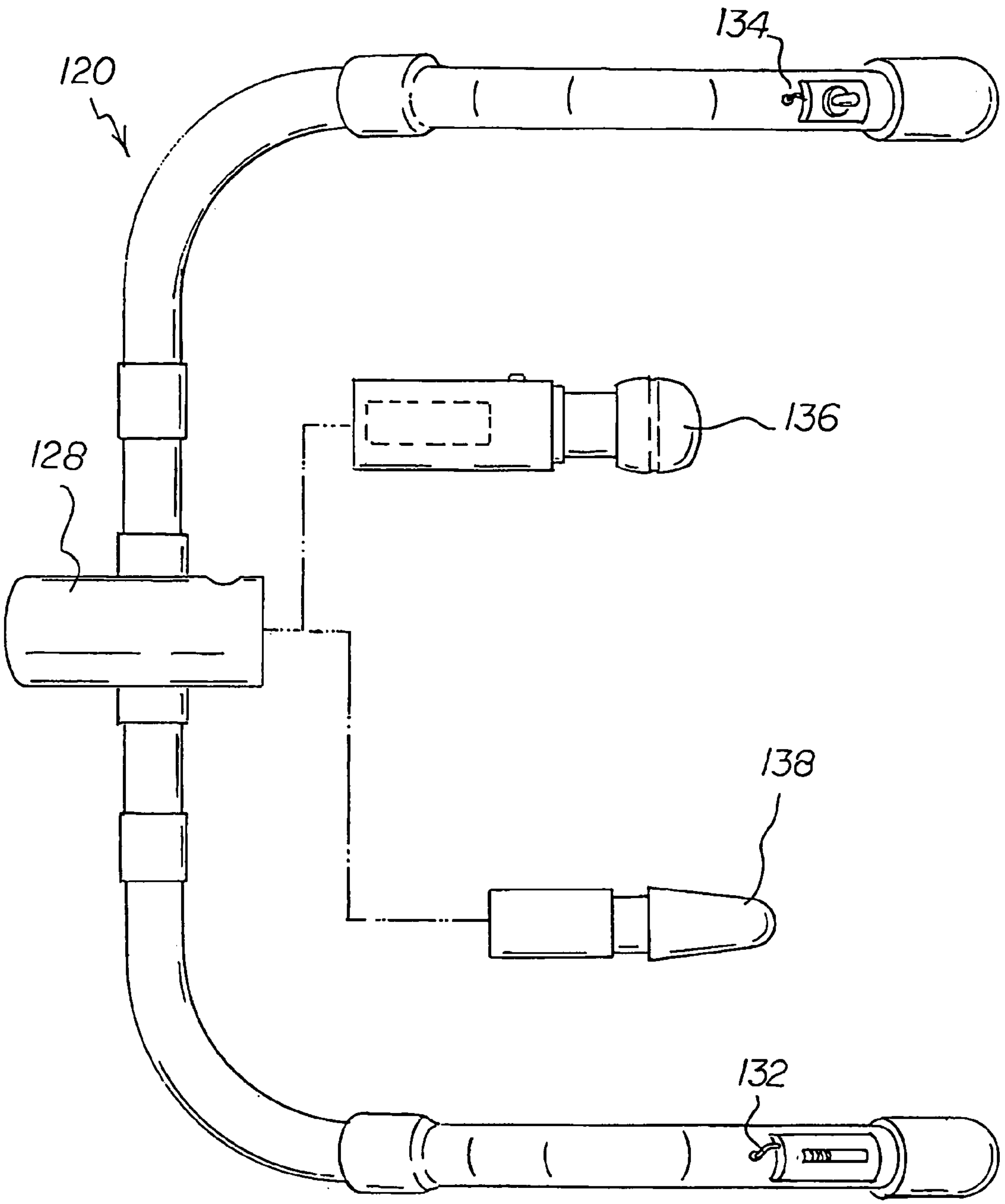
FIG. 10 is a plan view, partially exploded, taken along line 10—10 of FIG. 6.

FIG. 8 is a side elevational view of an even further alternate embodiment of the invention. In this embodiment, the system 100 includes two dildos facing forwardly as in the FIG. 5 embodiment and two dildos facing rearwardly as in the FIG. 7 embodiment. More specifically, the FIG. 8 embodiment includes a coupling component 102 with laterally extending ends for the handles and longitudinally extending ends 104 and an upwardly extending end. This embodiment also includes a supplemental coupling component 106 with longitudinally extending ends 108 and a downwardly extending end coupled to the upwardly extending end of the coupling component 104. A lower forward dildo 110 and a lower rearward dildo 112 are coupled in axial alignment to the coupling component 102. A upper forward dildo 114 and a lower rearward dildo 116 are coupled in axial alignment to the supplemental coupling component 108.

FIG. 9 is a side elevational view of the final alternate embodiment of the invention. The final embodiment of the invention is a system 120. Such system includes a coupling component 122 with laterally extending ends for handles and a longitudinal extending ends 124 and an upwardly extending end 126. The upwardly extending end terminates in longitudinal extending ends 128. A hollow joining component 130 couples the rearward ends of the upper and lower longitudinal components. Electric lines 132, 134 have first ends coupled to dildos 136, 138 which are removably secured to vibrators at the forward ends of the upper and lower coupling components. The electric lines have second end secured to the handles adjacent to the free ends of the handles. Line 132 has a variable speed capability while line 134 has an off/on capability. The switches are under the control of the primary user.

In operation and use, the system is preferably placed, with its coupling component and its ends, on a horizontal surface such as a bed or floor. The user then sits facing the system with the dildo or dildos facing the vagina and/or anus of the user and then grasps the grips. The user then moves the system through the handled in a reciprocating manner with respect to the vagina and/or anus for exercise which is stimulating and healthful.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A personal exercise system for allowing a user to perform a sexual exercise in a stimulating and healthful manner comprising, in combination:

a T-shaped coupling component with laterally extending ends and a rearwardly extending end, the coupling component being positionable on a horizontal support surface adjacent to a user;

a U-shaped intermediate component in a vertical plane with a free lower end and a free upper end formed with male threads, and a lower joining piece connecting the lower end of the intermediate component and the rearwardly extending end of the coupling component;

a generally cone shaped dildo being in a generally linear configuration located above, and parallel with, the rearwardly extending end and the lower joining piece, the dildo having an interior end and a free exterior end located above the rearwardly extending end of the T-shaped coupling component, and an upper joining piece having a rearward end formed with female threads removably coupled to the male threads of the intermediate component, the upper joining piece having a forward end formed with a set screw there adjacent for removable securling the dildo and the upper joining piece to the male threads of the intermediate component;

a handle extending outwardly and upwardly from each laterally extending end of the T-shaped coupling component, each handle having an upper arcuate portion with a free upper end and a lower linear component with an interior end coupled to a laterally extending end of the T-shaped coupling component, the handle and laterally extending ends of the T-shaped coupling component being located in a vertical plane perpendicular the horizontal plane containing the intermediate member;

a grip fabricated of an elastomeric material removably positioned on each free end of the handle, each grip extending upwardly and rearwardly away rom the vertical plane containing the handle, the grips being at an elevation above the dildo with the free end of the dildo being at an elevation adjacent to the midpoint of the arcuate portion of the handle; and a supplemental dildo with a hemispherical free end adapted to be used as an alternative to the dildo with the generally conical free end.

2. A personal exercise system comprising:

a coupling component with laterally extending ends and a rearwardly extending end;

an intermediate component with a free lower end and a free upper end coupling to the rearwardly extending end of the coupling component;

a dildo located above the rearwardly extending end, the dildo having an interior end and a free exterior end located above the rearwardly extending end of the coupling component removable coupling the upper intermediate component to the dildo; and a handle extending outwardly and upwardly from each laterally extending end of the coupling component, each handle having an upper arcuate portion with a free upper end and a lower linear component with an interior end coupled to a lateral extending end of the coupling component.

3. The system as set forth in claim 2 wherein the lower end of the intermediate component and the rearwardly extending end of the coupling component are in a horizontal plane during operation and use.

4. The system as set forth in claim 2 and further including a grip positioned on each upper free end of the handle remote from the coupling component, each grip extending upwardly and rearwardly, the grips being at an elevation above the dildo with the free end of the dildo being at an elevation adjacent to the midpoint of the handle.

5. The system as set forth in claim 2 and further including a grip positioned on each upper free ends of the handle remote from the coupling component, with the intermediate component formed to have a supplemental bend for locating the dildo at an elevated height whereby each grip extends upwardly and rearwardly, the grips having a lower end being at an elevation adjacent to the dildo.

6. The system as set forth in claim 2 and further including a grip positioned on each upper free ends of the handle remote from the coupling component, with the intermediate component formed to support an upper dildo and a supplemental projection formed to support a supplemental dildo beneath the upper dildo and for locating the dildos at heights, one above and one below the lower ends of the grips.

7. The system as set forth in claim 2 and further including supplemental coupling component having longitudinally extending ends facing forwardly and rearwardly and a downwardly extending end coupled to the upwardly extending end, the system further including a forwardly extending dildo for a primary user and a rearwardly extending dildo for another user.

8. The system as set forth in claim 2 wherein the handles include similarly configured interior components coupled interiorly to the laterally extending ends of the coupling component and similarly configured exterior components coupled interiorly to the interior components, the exterior components have generally directed free ends for being held by a primary user.

9. The system as set forth in claim 2 and further including includes two dildos facing forwardly and two dildos facing rearwardly.

10. The system as set forth in claim 2 and further including at least one electric line having a first end coupled to a dildo which is removably secured to a vibrator, the electric line having a second end secured to a handle adjacent to a free end with a switch under the control of the primary user.

* * * * *